(12) United States Patent
Herrmann et al.

(10) Patent No.: US 8,514,044 B2
(45) Date of Patent: Aug. 20, 2013

(54) MEDICAL EXAMINATION OR TREATMENT DEVICE

(75) Inventors: Norbert Herrmann, Ebnath (DE); Andreas Limmer, Seybothenreuth (DE)

(73) Assignee: Siemens Aktiengesellschaft, München (DE)

( * ) Notice: Subject to any disclaimer, the term of this patent is extended or adjusted under 35 U.S.C. 154(b) by 0 days.

(21) Appl. No.: 13/213,961

(22) Filed: Aug. 19, 2011

(65) Prior Publication Data
US 2012/0212308 A1 Aug. 23, 2012

(30) Foreign Application Priority Data
Aug. 25, 2010 (DE) .................... 10 2010 035 395

(51) Int. Cl.
*H01F 7/02* (2006.01)
*H02K 41/02* (2006.01)
(52) U.S. Cl.
USPC ........................................ 335/306; 310/12.01
(58) Field of Classification Search
USPC ................ 335/302, 306; 310/12.09, 12.11
See application file for complete search history.

(56) References Cited

U.S. PATENT DOCUMENTS

| | | | | |
|---|---|---|---|---|
| 5,598,044 A * | 1/1997 | Satomi et al. | | 310/12.24 |
| 5,854,521 A * | 12/1998 | Nolle | | 310/216.004 |
| 6,119,034 A * | 9/2000 | Herrmann et al. | | 600/427 |
| 6,241,671 B1 * | 6/2001 | Ritter et al. | | 600/427 |
| 6,408,987 B2 * | 6/2002 | Morishita | | 187/292 |
| 6,609,826 B1 | 8/2003 | Fujii et al. | | |
| 6,700,229 B2 * | 3/2004 | Sadarangani et al. | | 310/12.12 |
| 6,717,297 B2 * | 4/2004 | Sadarangani et al. | | 310/14 |
| 6,731,029 B2 * | 5/2004 | Shikayama et al. | | 310/58 |
| 6,864,647 B2 * | 3/2005 | Duncan et al. | | 318/114 |
| 6,879,064 B2 * | 4/2005 | Kobayashi et al. | | 310/12.01 |
| 6,879,066 B2 * | 4/2005 | Hashimoto et al. | | 310/12.24 |
| 7,170,202 B2 * | 1/2007 | Watarai et al. | | 310/12.25 |
| 7,768,158 B2 * | 8/2010 | Kitamura et al. | | 310/12.22 |
| 8,083,389 B2 * | 12/2011 | Helmreich et al. | | 362/572 |
| 2002/0003854 A1 * | 1/2002 | Ivan et al. | | 378/20 |
| 2003/0234584 A1 * | 12/2003 | Miyata | | 310/12 |
| 2005/0029877 A1 * | 2/2005 | Harned et al. | | 310/12 |
| 2007/0052302 A1 * | 3/2007 | Cheung et al. | | 310/12 |
| 2007/0176505 A1 * | 8/2007 | Trzynadlowski et al. | | 310/114 |
| 2010/0049038 A1 * | 2/2010 | Florent et al. | | 600/425 |
| 2010/0210939 A1 * | 8/2010 | Hartmann et al. | | 600/424 |
| 2011/0122990 A1 * | 5/2011 | Dafni | | 378/4 |

FOREIGN PATENT DOCUMENTS

DE 602 07 625 T2 8/2006

OTHER PUBLICATIONS

German Office Action dated Jun. 6, 2011 for corresponding German Patent Application No. DE 10 2010 035 395.7 with English translation.

* cited by examiner

*Primary Examiner* — Alexander Talpalatski
(74) *Attorney, Agent, or Firm* — Lempia Summerfield Katz LLC

(57) ABSTRACT

A medical examination or treatment device including a C-arm that is guided movably along an arc path on a bracket via a mechanical guidance device is provided. Magnet elements are provided on the C-arm. Magnetic field generation elements on the bracket interact together to create a magnetic field that moves the C-arm along the arc path.

14 Claims, 4 Drawing Sheets

MEDICAL EXAMINATION OR TREATMENT DEVICE

This application claims the benefit of DE 10 2010 035 395.7, filed on Aug. 25, 2010.

BACKGROUND

The present embodiments relate to a medical examination or treatment device including a C-arm that is guided movably along an arc path on a bracket via a mechanical guidance device.

Examination or treatment devices of this kind may take the form of X-ray devices, in which a radiation source is arranged on one end of the C-arm and a radiation receiver is arranged on another end of the C-arm. As the C-arm is guided movably along an arc path, the C-arm and an image capture device may be moved about an isocenter relative to a patient. A motorized drive is used to provide the motion (e.g., in the form of a motorized drive shaft that engages with a belt that is connected to the C-arm). In the case of a belt movement, an automatic movement of the C-arm, which is otherwise guided by guide rollers and the like, is provided.

In light of the considerable weight of the C-arm plus the components arranged on the C-arm, the motor may be substantially dimensioned, as the motor moves the entire mass. Very rapid rotations may also frequently be performed. High rates of acceleration are to be achieved, which is to be taken into account in the design of the motor.

Devices are also known, in which the C-arm is moved manually. The manual movement is awkward and laborious, and rapid changes of position may not be provided.

SUMMARY AND DESCRIPTION

The present embodiments may obviate one or more of the drawbacks or limitations in the related art. For example, a medical examination or treatment device having a more compactly dimensioned motorized drive is provided.

In one embodiment, a medical examination or treatment device includes magnet elements provided on a C-arm and magnetic field generation elements provided on a bracket. The magnet elements and the magnetic field generation elements, interacting with each other, create a magnetic field that moves the C-arm along an arc path.

In one embodiment, the medical examination or treatment device may be characterized (e.g., in addition to the motorized drive previously installed) by the integration of a further drive device (e.g., a supplementary drive device) that is based on an electrically motorized principle. The supplementary drive device has the effect of supporting the drive via a first motorized drive unit including the drive motor that, for example, drives a belt. The electrically motorized supplementary drive accordingly generates drive power that is no longer provided by the first drive. The result of this is that the first motorized drive or the motor provided for this purpose may be more compactly dimensioned and designed. The first motorized drive may no longer move the entire mass, but only part thereof even if, depending on the design, the major part. The other part is undertaken by the integrated second drive. Other than the possibility of smaller dimensions of the actual drive motor, a mechanical force introduced for movement on the C-arm is reduced, as the supplementary drive device works in a non-contacting manner via the interacting magnetic fields. The system is consequently more stable.

If no first motorized drive is provided, but the C-arm is manually moved, the manual work may be supported by an integrated electrically motorized supplementary drive or if appropriately designed, almost completely undertaken by the supplementary drive.

An equilibration of the system, depending on the embodiment, may not be adjusted and optimized in such a precise manner, which was previously necessary due to the requirement that with the brakes open, the C-arm is not to move on its own. In one embodiment, the C-arm may be fixed in a current position without further action by momentary operation of the supplementary electromagnetic drive device, even if the brakes that are provided are open.

One embodiment of the medical examination or treatment device is thus characterized by two separately operating drives (e.g., a first motorized drive that is mechanically and movably coupled to the C-arm via a motor and a second electrically motorized drive including the magnet elements and the magnetic field generation elements, which interact together) or in the case of a manually moved arm, has the supplementary drive.

A plurality of permanent magnets with alternating polarity may, for example, be provided as magnet elements on the C-arm on an outer periphery, and a plurality of coils separately suppliable with current may be provided on the bracket as magnetic field generation elements. An additional drive device may be created in the form of a synchronous motor using the plurality of permanent magnets and the plurality of coils. A plurality of separate coils connected in series are provided on the bracket. Current is applied to the plurality of separate coils in a consecutive manner for a guided arm movement, so that a traveling magnetic field that runs along the plurality of separate coils arises. The plurality of separate coils has a motion component that, as a result of the interaction with the permanent magnets provided on the arm side, is transferred to the arm. The permanent magnets are, for example, arranged in groove- or pocket-shaped recesses on the C-arm and, consequently, in a correspondingly integrated position.

In one embodiment, the magnetic field generation elements provided on the bracket side (e.g., the coils provided on the stator side) are movable relative to the C-arm in order to be able to offset any distance tolerances to the magnet elements (e.g., the permanent magnets arranged on the arm side). The magnetic field generation elements (e.g., the coils) may be mounted movably relative to the C-arm against a reset force of one or a plurality of spring elements. The magnetic field generation elements may, for example, be arranged on a common bearing plate, on which the magnetic field generation elements may be pre-mounted. The magnetic field generation elements may thus be installed as a coil package on the arm side.

To amplify the fields generated via the individual coils, the individual coils may be equipped with iron cores in order to concentrate the flow and be able to maximize the generated interacting fields.

In one embodiment, two coils are arranged as a pair on two opposite sides of the bracket, accommodating the C-arm between the two coils. Viewed horizontally, two coils in each case lie opposite each other in a horizontal plane. Current may be applied to the coils synchronously, such that effectively on two sides of the arm with the permanent magnets provided on the two sides of the atm (e.g., on both sides of the arm, viewed horizontally, oppositely located permanent magnets are also provided), a magnetic field linkage that makes it possible to transfer even higher drive forces as a result of the field interaction than when using just one coil and one permanent magnet is created.

DETAILED DESCRIPTION OF THE DRAWINGS

Figure 1:
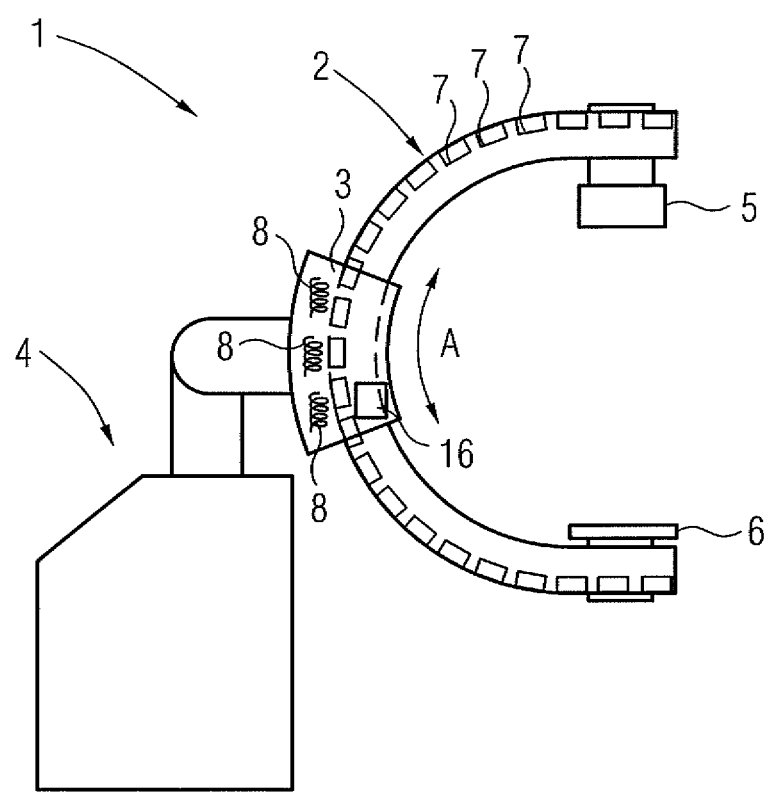
FIG. 1 shows a schematic diagram of one embodiment of an examination or treatment device.

FIG. 1 shows a schematic diagram of one embodiment of a medical examination or treatment device 1. The medical examination or treatment device 1 includes a C-arm 2 and a bracket 3. In the example shown in FIG. 1, the medical examination or treatment device 1 is configured on a floor stand 4 in height- and laterally-adjustable form. In another embodiment, the medical examination or treatment device 1 may be arranged on a ceiling stand.

Arranged on the C-arm 2 are a radiation source 5 and a radiation receiver 6 in order to capture radiation images (e.g., X-ray images). The C-arm 2 is movably arranged along the bracket 3, as represented by arrow A. During operation, the C-arm 2 may be fixed.

The C-arm 2 is moved manually or via a motorized drive (e.g., a main drive) that is addressed in greater detail below with reference to FIG. 3. In each case, an additional electrically motorized drive is provided. In the case of a manually movable C-arm, the additional electrically motorized drive supports the manual actuation or largely replaces the manual actuation, while the additional electrically motorized drive functions as an auxiliary drive if a motorized main drive is employed.

Magnet elements 7 in the form of permanent magnets, for example, may be arranged on the C-arm 2. The magnet elements 7 are arranged on the C-arm 2 in an area of an outer periphery (e.g., on the perimeter or on the lateral circumference). Arranged on the bracket 3 (e.g., shown only in schematic form) are magnetic field generation elements 8 (e.g., electromagnets) in the form of individual electromagnets, for example. The magnetic field generation elements 8 each include a coil and an iron core. The electromagnets 8 serve as exciter magnets for the generation of a magnetic field that interacts with the permanent magnets 7. The electromagnets 8 may be actuated separately and may be arranged on the bracket 3 in linear succession relative to a direction of movement of the C-arm 2. In the case of corresponding alternate actuation of the individual electromagnets 8, a magnetic field traveling along the bracket 3 is created. The magnetic field traveling along the bracket 3, as known from the functional principle of an electric motor, interacts with the permanent magnets 7 on the arm side, so that the permanent magnets 7 follow the traveling magnetic field. As a result, a movement of the C-arm 2 is effected. The C-arm 2 is mechanically guided on the bracket 3 by bearing and guidance devices (e.g., roller and plain bearings) that are not shown in greater detail in FIG. 1.

The permanent magnets 7 are arranged on the C-arm 2 at defined distances (e.g., with alternating polarity), and the permanent magnets 7 or the C-arm 2, respectively, represent an armature. The electromagnets 8 are arranged, as described, in the bracket 3 of the C-arm 2. The electromagnets 8, in the form of the described 3-phase windings, assume the function of a stator. In one embodiment, the permanent magnets 7 are arranged in groove- or pocket-shaped recesses (e.g., C-grooves) distributed around the periphery on the C-arm 2.

The structural principle of this integrated electrically motorized drive is that of a synchronous motor, via which the C-arm movement may be supported. In order to start up, the synchronous motor may use a starting aid. In the case of a manually moved C-arm 2, the starting aid is provided by an operator, who turns the C-arm 2. As a result of the movement of the permanent magnets 7 relative to the electromagnets 8, the electric motor may take over. If the main drive is provided, the main drive undertakes the startup movement, and the supplementary drive provides support.

The electromagnets 8 are actuated accordingly by a control device, which is not shown in greater detail, so that the traveling magnetic field is generated. The possibility of commutation via a commutator exists so that the direction of the generated fields and the drive direction may be varied.

Figure 2:
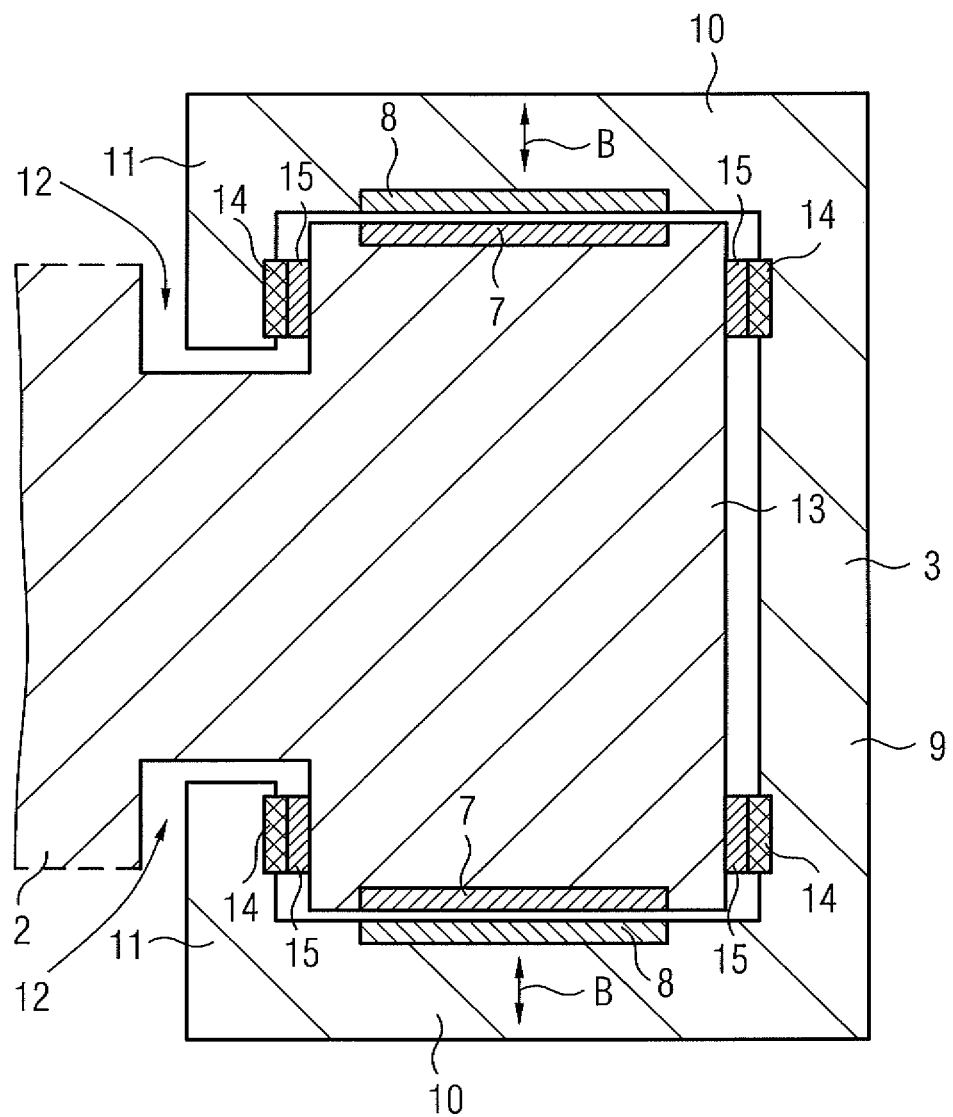
FIG. 2 shows a sectional view through an area of a bearing of a C-arm in a bracket of one embodiment of the examination or treatment device from FIG. 1.

FIG. 2 shows a sectional view through the C-arm 2 and the bracket 3 in the form of a schematic diagram, in order to represent a possible alternative arrangement of the permanent magnets 7 and the electromagnets 8. The bracket 3 is essentially embodied in U-shaped form, having a base limb 9, two side limbs 10 and two frontal limbs 11. The C-arm 2 is correspondingly contoured at an end facing the bracket 3, having two lateral grooves 12, in which the frontal limbs 11 engage. The C-arm 2 is accommodated in the bracket 3 with an extended section 13.

Figure 4:
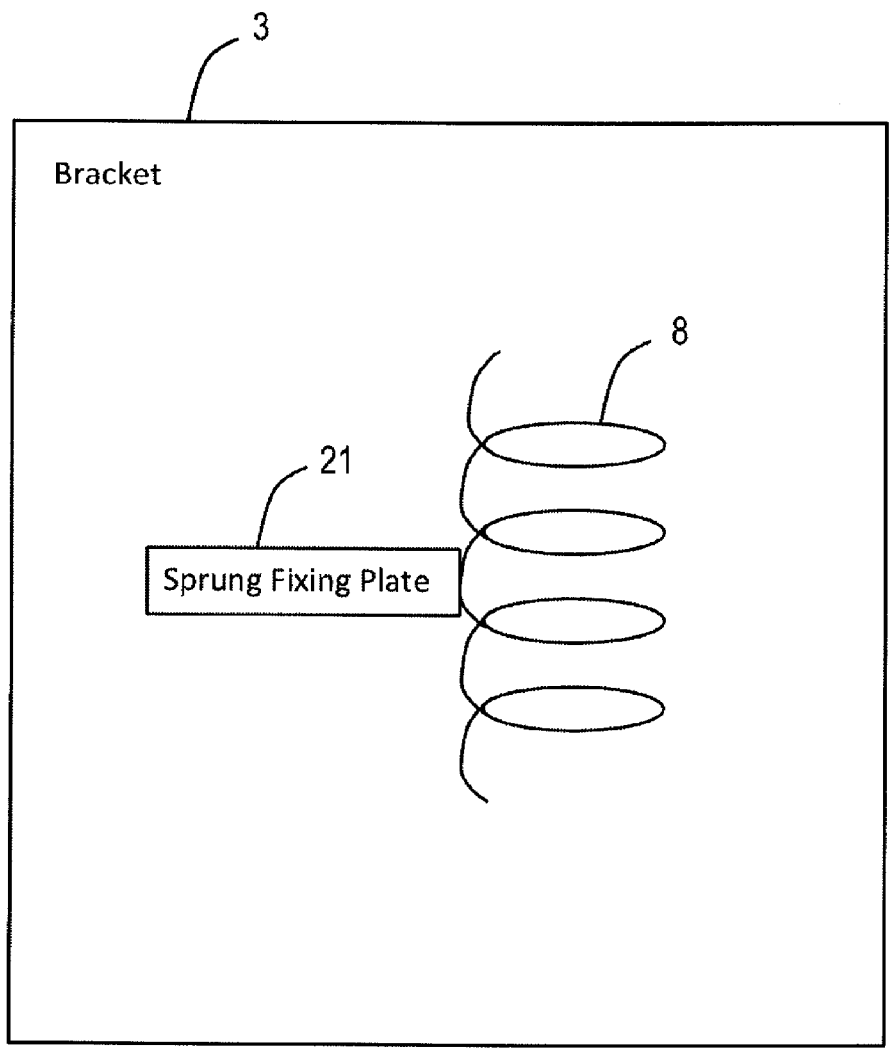
FIG. 4 shows exemplary electromagnets movably mounted to a bracket.

Arranged distributed over the length of the bracket 3 on inner sides of the side limbs 10 are the magnetic field generation elements 8 in the form of, for example, the electromagnets. Each of the electromagnets 8 includes a coil and an iron core. The electromagnets 8 are, as represented by the respective double arrow B, movably mounted in order to take up any variation in distances relative to the C-arm 2 that may result from the arm movement. A distance from the electromagnets 8 to the integrated permanent magnets 7 on the C-arm 2 lying opposite the electromagnets 8 essentially remains constant. As shown in FIG. 4, electromagnets 8 are, for example, accommodated on a sprung fixing plate 21 or similar. Movement of the sprung fixing plate automatically adjusts, depending on the relative position of the C-arm 2 to the bracket 3. The automatic adjustment may be effected using a suitable motion linkage from the C-arm 2 to the sprung fixing plate or similar device. The electromagnets 8 distributed over the length of the bracket 3 and the permanent magnets 7 arranged distributed across lateral lengths of the C-arm 2 are located immediately opposite to each other so that fields generated via the electromagnets 8 may interact with the permanent magnets 7 for the drive.

The bearing or guidance of the C-arm 2 takes place using corresponding sliding and roller elements that are arranged on the C-arm 2 and the bracket 3. In the example shown, corresponding sliding or roller elements 14 (e.g., guide rollers) are arranged on the base limb 9 of the bracket 3. Further sliding or roller elements 15 (e.g., slide rails) that run on the sliding or roller elements 14 (e.g., the guide rollers) are arranged on the outside of the C-arm 2. Corresponding sliding or roller elements 14, 15 are arranged on another side of the bracket 3 (e.g., on the frontal limbs 11) or of the C-arm 2. In this way, secure guidance of the C-arm 2 and the bracket 3 is provided. In other embodiments, further guidance elements may be integrated.

As FIG. 1 shows, a braking device 16 that fixes the C-arm 2 in a current position may also be provided. This serves, in the event of an incomplete equilibration of the C-arm 2, from which autonomous movement of the C-arm 2 may result in the case of a released braking device 16, to prevent the autonomous movement from happening when at rest. In the case of incomplete equilibration and manual movement of the C-arm 2, the electrically motorized drive is used. Without further action, the electrically motorized drive may allow for a corresponding incorrect equilibration and may perform the C-arm movement in a corresponding braked manner, without the user having to take any manual action after rotation of the arm. The electrically motorized drive then functions as the sole drive. In the case of a balanced arm, this is possible without further action.

Figure 3:
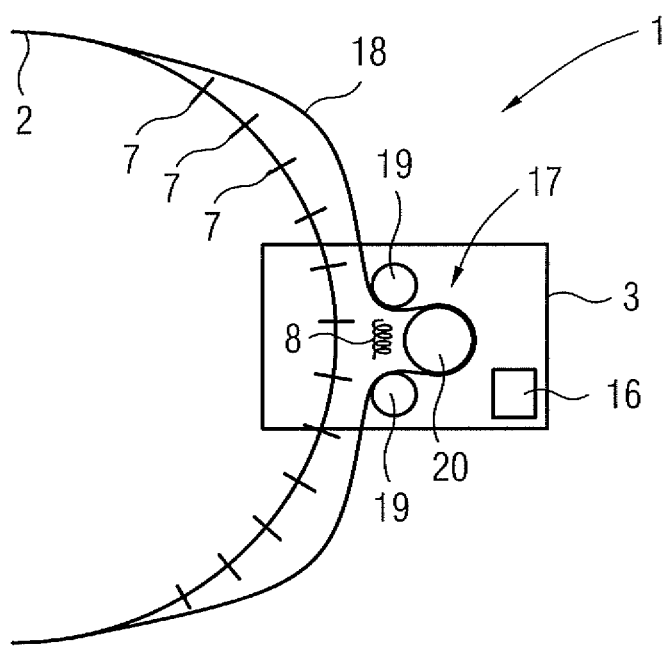
FIG. 3 shows a schematic diagram of one embodiment of an examination or treatment device with a supplementary belt drive.

FIG. 3 shows a schematic diagram of one embodiment of an examination or treatment device 1. The examination or treatment device 1 includes the C-arm 2 and the bracket 3. The magnet elements 7 are arranged on the C-arm 2, and the magnetic field generation elements 8 (e.g., the electromagnets) are arranged on the bracket 3. In addition to the electrically motorized drive that, for example, functions solely as an auxiliary drive, a motorized main drive 17 is provided. The motorized main drive 17 includes a belt 18 that acts on the C-arm 2 with two ends and is guided into the bracket 3. The belt 18 is guided in the bracket 3 via two deviation rollers 19 and runs over a drive shaft or drive roller 20 that is coupled with a drive motor and rotated via the drive motor. Upon rotation of the drive motor, an automatic movement of the C-arm is effected as a result of the belt 18 being driven. The braking device 16, which brakes the drive shaft 20, is provided in order to fix the C-arm 2 in position.

The integration of the electrically motorized drives makes it possible to design the drive motor or the entire main drive 17 to be smaller, as the drive motor or the entire main drive 17 no longer needs to drive the whole load of the C-arm (e.g., to provide the whole drive torque), but only part thereof, with the remaining part being assumed by the electrically motorized drive.

Even if a belt drive is provided in FIG. 3 as the main drive 17, other drive concepts may be provided as the main drive 17. In light of the additional integration of the electrically motorized auxiliary drive, the main drive 17 may be embodied with smaller dimensions.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A medical examination or treatment device comprising:
a bracket comprising a base and two sides extending from the base;
a mechanical guidance device;
a C-arm that is guided movably along an arc path on the bracket via the mechanical guidance device;
magnet elements provided on the C-arm; and
magnetic field generation elements provided on inner surfaces of the two sides of the bracket,
wherein the magnet elements and the magnetic field generation elements interacting together create a magnetic field that moves the C-arm along the arc path,
wherein the magnet elements comprise a plurality of permanent magnets with alternating polarity, the plurality of permanent magnets being disposed on an outer periphery of the C-arm,
wherein the magnetic field generation elements comprise a plurality of coils separately suppliable with current, the plurality of coils being provided on the inner surfaces of the two sides of the bracket,
wherein two of the magnetic field generation elements are arranged as a pair on the inner surfaces of the two sides of the bracket, respectively, the inner surfaces being opposite of each other, and
wherein the C-arm is accommodated between the two magnetic field generation elements.

2. The examination or treatment device as claimed in claim 1, wherein the plurality of permanent magnets is arranged on the C-arm in groove-shaped or pocket-shaped recesses.

3. The examination or treatment device as claimed in claim 1, wherein the plurality of coils are movable relative to the inner surfaces of the two sides of the bracket, such that for a coil of the plurality of coils, a distance between the coil and a permanent magnet of the plurality of permanent magnets that lies opposite the coil remains substantially constant.

4. The examination or treatment device as claimed in claim 1, wherein the plurality of coils is movably mounted relative to the C-arm against a reset force of one or a plurality of spring elements.

5. The examination or treatment device as claimed in claim 1, wherein each coil of the plurality of coils includes an iron core.

6. The examination or treatment device as claimed in claim 1, wherein the magnetic field generation elements are movable relative to the inner surfaces of the two sides of the bracket, such that for a magnetic field generation element of the magnetic field generation elements, a distance between the magnetic field generation element and a magnet element of the magnet elements that lies opposite the magnetic field generation element remains substantially constant.

7. The examination or treatment device as claimed in claim 1, wherein the plurality of coils is movable relative to the C-arm.

8. The examination or treatment device as claimed in claim 2, wherein each coil of the plurality of coils includes an iron core.

9. The examination or treatment device as claimed in claim 3, wherein each coil of the plurality of coils includes an iron core.

10. The examination or treatment device as claimed in claim 4, wherein each coil of the plurality of coils includes an iron core.

11. The examination or treatment device as claimed in claim 2, wherein two of the magnetic field generation elements are arranged as a pair on the inner surfaces of the two sides of the bracket, respectively, the inner surfaces being opposite of each other, and
wherein the C-arm is accommodated between the two magnetic field generation elements.

12. The examination or treatment device as claimed in claim 3, wherein two of the magnetic field generation elements are arranged as a pair on the inner surfaces of the two sides of the bracket, respectively, the inner surfaces being opposite of each other, and
wherein the C-arm is accommodated between the two magnetic field generation elements.

13. The examination or treatment device as claimed in claim 4, wherein two of the magnetic field generation elements are arranged as a pair on the inner surfaces of the two sides of the bracket, respectively, the inner surfaces being opposite of each other, and
wherein the C-arm is accommodated between the two magnetic field generation elements.

14. The examination or treatment device as claimed in claim 5, wherein two of the magnetic field generation elements are arranged as a pair on the inner surfaces of the two sides of the bracket, respectively, the inner surfaces being opposite of each other, and wherein the C-arm is accommodated between the two magnetic field generation elements.

\* \* \* \* \*